US009833581B2

(12) United States Patent
Eggert et al.

(10) Patent No.: US 9,833,581 B2
(45) Date of Patent: Dec. 5, 2017

(54) MEDICAL DEVICE AND METHOD FOR LIMITING THE USE OF THE MEDICAL DEVICE

(71) Applicant: SANOFI-AVENTIS DEUTSCHLAND GMBH, Frankfurt am Main (DE)

(72) Inventors: Ilona Eggert, Frankfurt am Main (DE); Michael Caspers, Frankfurt am Main (DE); Richard James Vincent Avery, Gloucestershire (GB); Shane Alistair Day, Warwickshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/356,943

(22) PCT Filed: Nov. 15, 2012

(86) PCT No.: PCT/EP2012/072792
§ 371 (c)(1),
(2) Date: May 8, 2014

(87) PCT Pub. No.: WO2013/072443
PCT Pub. Date: May 23, 2013

(65) Prior Publication Data
US 2014/0309588 A1 Oct. 16, 2014

(30) Foreign Application Priority Data
Nov. 18, 2011 (EP) ..................... 11189722

(51) Int. Cl.
*A61M 5/50* (2006.01)
*A61M 5/20* (2006.01)
*A61M 5/24* (2006.01)

(52) U.S. Cl.
CPC ............ *A61M 5/5086* (2013.01); *A61M 5/20* (2013.01); *A61M 5/24* (2013.01); *A61M 2205/273* (2013.01)

(58) Field of Classification Search
CPC ........ A61M 5/20; A61M 5/5086; A61M 5/24; A61M 5/14; A61M 5/31565; A61M 5/3157; A61M 5/31571
See application file for complete search history.

(56) References Cited

U.S. PATENT DOCUMENTS

| 533,575 A | 2/1895 | Wilkens |
| 4,515,590 A * | 5/1985 | Daniel .................. A61D 1/025 604/144 |

(Continued)

FOREIGN PATENT DOCUMENTS

| EP | 0293958 | 12/1988 |
| EP | 0937471 | 8/1999 |

(Continued)

OTHER PUBLICATIONS

International Search Report for Int. App. No. PCT/EP2012/072792, completed Jan. 21, 2013.

(Continued)

*Primary Examiner* — Quynh-Nhu H Vu
*Assistant Examiner* — Nilay Shah
(74) *Attorney, Agent, or Firm* — McDonnell Boehnen; Hulbert & Berghoff LLP

(57) ABSTRACT

A method for detecting a limit of use of a medical device is presented having the steps of starting a timer of a medical device when the medical device is used for the first time, detecting the limit of use of the medical device and indicating the limit of use of the medical device. The limit of use is reached when at least one of a first criterion and a second criterion is met, wherein the first criterion is that the timer (Continued)

reaches or exceeds a time limit and wherein the second criterion is that at least one operation of a drive train of said medical device reaches or exceeds a limit.

10 Claims, 12 Drawing Sheets

(56) References Cited

U.S. PATENT DOCUMENTS

| | | | |
|---|---|---|---|
| 4,613,328 A | 9/1986 | Boyd | |
| 4,652,261 A | 3/1987 | Mech et al. | |
| 5,226,895 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,126,642 A * | 10/2000 | Kriesel | A61M 5/1424 604/131 |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 * | 7/2006 | Fiechter | A61M 5/31553 417/63 |
| 2007/0021715 A1 * | 1/2007 | Kohlbrenner | A61M 5/20 604/67 |
| 2008/0200747 A1 * | 8/2008 | Wagner | A61M 5/14546 600/5 |
| 2009/0076443 A1 | 3/2009 | Slate et al. | |
| 2009/0275916 A1 | 11/2009 | Harms et al. | |

FOREIGN PATENT DOCUMENTS

| | | |
|---|---|---|
| EP | 0937476 | 8/1999 |
| JP | S63-286166 A | 11/1988 |
| JP | 2006-507856 A | 3/2006 |
| JP | 2006-187628 A | 7/2006 |
| WO | 99/38554 | 8/1999 |
| WO | 01/10484 | 2/2001 |
| WO | 2004/010231 | 1/2004 |
| WO | 2006/124775 | 11/2006 |
| WO | 2008/128074 | 10/2008 |
| WO | 2010/073452 A1 | 7/2010 |

OTHER PUBLICATIONS

Chinese Office Action for CN Application No. 201280067446.5, dated Apr. 25, 2016.

Chinese Search Report for CN Application No. 201280067446.5, dated Apr. 11, 2016.

Japanese Office Action for JP Application No. 2014-541671, mailed Nov. 15, 2016.

* cited by examiner

MEDICAL DEVICE AND METHOD FOR LIMITING THE USE OF THE MEDICAL DEVICE

CROSS REFERENCE TO RELATED APPLICATIONS

The present application is a U.S. National Phase Application pursuant to 35 U.S.C. §371 of International Application No. PCT/EP2012/072792 filed Nov. 15, 2012, which claims priority to European Patent Application No. 11189722.9 filed Nov. 18, 2011. The entire disclosure contents of these applications are herewith incorporated by reference into the present application.

TECHNICAL FIELD

The current invention relates to a method for detecting a limit of use of a medical device comprising the steps of starting a timer of a medical device when said medical device is used for the first time, detecting the limit of use of the medical device and indicating the limit of use of the medical device. The invention also relates to a medical device for performing a method according to the invention.

BACKGROUND

For certain devices it is necessary to limit the life time of the device, although the devices might still be operable. This is in particular the case when the proper functioning of a device is mandatory for the physical integrity of the user of the very device, for example. This is especially the case for medical devices, since the correctness of the presented or evaluated data by the device or the dose of a certain drug administered by the device is in many cases mandatory for the health of the patient. Thus, devices which cannot be permanently checked or inspected can be deactivated after a fixed amount of time to prevent major malfunctions. For instance, it is known from the state of the art to use the elapsed time since the first use of a medical device to limit the lifetime of the medical device by disabling the device after the elapsed time since the first use has reached a certain limit.

In this way, it is achieved that in many cases any serious errors due to unavoidable wear in form of material fatigue, for example, are prevented from appearing in the first place.

SUMMARY

The present patent application relates in particular to medical devices for delivering at least two drug agents from separate reservoirs. Such drug agents may comprise a first and a second medicament. The medical device includes a dose setting mechanism for delivering the drug agents automatically or manually by the user.

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

To determine the life time, after which such a device is deactivated, often assumptions about typical uses are made, for example 4 doses per day of 40 units per dose, a unit being a defined quantity of medicament, for example an international unit, which is frequently used as a measure for insulin. This, however, does not cover the worst case of high dose users.

Due to the importance of safety for such medical devices, there is a demand for further improving the safety of such devices. It would be possible to reduce the allowed life time of a device in order to further reduce the probability of an error due to wear, for example. This is disadvantageous though, since this would also increase the number of "premature" deactivations. These devices are being deactivated even though they would still be operable without any error for a longer time.

In view of the aforementioned, the invention faces the technical problem of providing a method and a medical device, the safety of which is further increased and at the same time the limit of use is not prematurely induced.

According to a first aspect of the present invention, the technical problem is solved by a generic method wherein the limit of use is reached when at least one of a first criterion and a second criterion is met, wherein the first criterion is that the timer reaches or exceeds a time limit and wherein the second criterion is that at least one operation of a drive train of said medical device reaches or exceeds a limit.

By providing not only a first criterion, which is fulfilled, when the timer reaches or exceeds a time limit, but also a second criterion, which can be fulfilled independent of the first criterion and in particular before the first criterion is fulfilled, the safety of the device can be improved. By limiting at least one operation of a drive train an additional element of the usage of the medical device is taken into account for the detection of the limit of use of the medical device. A more precise estimation of the wear and use of the device can be provided in this way resulting in the possibility to indicate the limit of use of the medical device earlier than the time limit of the first criterion and at the same time allowing the time limit of the first criterion to be set more generously without risking errors of the device due to wear and use, since these aspects are additionally considered by the second criterion.

Furthermore, an individual limit of use is provided in this way, providing the maximum life time of the device for a user without risking the safety of the device.

The degree of safety can be adjusted by providing more criteria to check for. Generally, it will not be expedient to check as many criterions as possible, since this takes up resources and space for adequate sensors, for example. Though, it is possible to choose the criterions to check and elements to monitor, which represent the "weakest link" in the chain of components in order to provide maximum safety with least effort.

When determining the limit of use, the fulfillment of one of two or more criteria is sufficient to consider the device as having reached its limit of use. When the limits of both or all of the criteria are reached, the medical device is also considered as having reached the limit of its use.

A drive train can in particular comprise elements like a gearing arrangement, an electromechanical assembly, such as a stepper motor, a piston rod, a drive shaft and/or similar elements. The drive train can in particular be used to eject a fluid or medicament out of a reservoir by providing a pressure on a bung, for example.

By taking into account at least one operation of a drive train of the medical device, a particularly precise estimation of the actual wear and thus the actual risk of a failure can be achieved, since the operation of the drive train is tightly connected to the actual use of the device. The drive train may be prone to wear. For example, during every dose dispensing the drive train needs to be operated. From an operation of the drive train not only the general fact, that a dose was dispensed by the medical device, can be derived. Moreover, the units as a measure of the actual size of a dose can be counted, for example. If the number of doses is counted, the size of each dose may or may not be accounted for. If the actual units dispensed are counted though, the estimation of the wear of the medical device can be more precise compared to when merely the dispensing is accounted for, since for instance multiple smaller doses can effect the same movement of the drive train as a single larger dose. It is in particular possible to count operations of an electromechanical assembly of the drive train, such as motor steps, running time and/or the like.

It is especially advantageous to consider an operation of the drive train compared to other operations, such as merely detecting that a dose delivery has happened, since the operations of the drive train provide more detailed information about the device.

The step indicating the limit of use is understood to mean that the user can be informed by the limit of use in form of display, audio signals, or other signals, for example. However, it is also possible that any further use of the medical device is prevented by deactivating or blocking the device and thus the limit of use is implicitly indicated to the user, since no further use is possible. Both, a prevention of use and an explicit signal to the user might be provided as an indication of the limit of use, as well. It is also possible to provide a warning signal to the user first but allowing further use of the device and only when a second limit is reached or more than one criterion is fulfilled prevent the use of the device.

By limiting the use, it is possible to either limit the use temporarily or constantly. Limiting the use on the one hand constantly or irreversibly usually happens after the device has reached its lifetime, because a proper functioning of the device cannot be guaranteed anymore. Limiting the use only temporarily or reversibly on the other hand, provides the possibility to prevent an overuse in a short period of time, for example, and thus preventing the medical device from overheating. After a certain time, for example after 15 minutes or a day, the limit can be canceled. It is especially preferred, when the both a reversible and an irreversible limit is provided.

There can be more than two criteria which are taken into account when detecting the limit of the medical device. It is possible to detect the limit of use of the medical device when only a single criterion is fulfilled, when multiple criteria are fulfilled or when all criteria are fulfilled. One criterion might comprise multiple limits relating to different operations of the drive train, as well. There may also be multiple criteria relating to an operation of the drive train.

A typical time limit for the timer is between one and three years, in particular two years. The limit is preferably predefined, but it is possible to influence this limit depending on use of the device or the type of interfaces connected to the medical device, for example.

When it is stated that an operation or action reaches a limit, it is meant that a count limit of single operations or actions is reached or that a time limit of total operating time of the respective operations or actions is reached. It is further possible to consider both, the count limit and the time limit.

It is further possible to either add operation counts or operating times directly after the respective operation to a total counter or timer. Alternatively, the operating counts and/or times can be added after a fixed period, for example a day.

It is further possible to calculate the respective number of operations or operating times from a saved dose delivery history of the medical device.

According to a first embodiment of the method according to the invention, one operation of the drive train is the number of steps of an electromechanical assembly.

The electromechanical assembly is in this case preferably a stepper motor. By choosing the number of steps as the at least second criterion, a very precise estimation of the use of the medical device can be achieved, since one dose usually consists of multiple units and one unit usually consists of multiple steps. By limiting the number of steps of the electromechanical assembly the usage of the medical device is taken into account for the detection of the limit of use of the medical device. A particularly precise estimation of the wear and use of the device can be provided in this way resulting in the possibility to indicate the limit of use of the medical device earlier than the time limit of the first criterion and at the same time allowing the time limit of the first criterion to be set more generously without risking errors of the device due to wear and use, since these aspects are additionally considered by the second criterion.

The steps of an electromechanical assembly may be counted as they are instructed or requested from the electromechanical assembly. This provides a particularly easy implementation, since a control unit can for example count the number of steps sent to the electromechanical assembly via a control signal, for example. No further adaption of the hardware is necessary.

The steps of an electromechanical assembly may also be counted as they are detected. This way it can be made sure, that only actual movement of the electromechanical assembly is considered. For example, on the one hand it might be the case that instructed steps are not executed because of a stalling of the motor or the blocking of the device. On the other hand, it might also be possible that the electromechanical assembly is moved even though no steps were requested. Thus a more precise measure of the use of the device can be provided in this way. The detection of the actual movement can be performed by a motion detector system, for example.

It is further possible to count the steps of the mechanical device during a dispense or during a rewind, meaning during the forward or the backward movement of the electromechanical assembly. It is also possible to count during both movements.

It is further advantageous, that the counted number is substantially independent from the speed of the electromechanical assembly, for example.

According to another embodiment of the method according to the invention, one operation of the drive train is the number of rewinds.

Rewinds are considered to be the refraction of a piston rod for example, which is used to push a fluid out of a reservoir or a cartridge. Generally, there is only a rewind operation if the respective cartridge or reservoir is empty and needs to be exchanged. Otherwise, there are conventionally only movements of the piston rod substantially in the forward direction in order to dispense the fluid. The impact of the piston rod or bung at the end of the rewind cycle can be used as a counter for a complete rewind operation, for example. It is advantageous though, that when the user for example "plays" with the device and opens a door of the medical device to the cartridge or presses the cartridge eject button, the rewinds taking place in these cases are also accounted for, even though no medicaments or fluids were dispensed. An additional degree of use which is accounted for in this way, which would otherwise not be considered, and thus further improves the safety of the medical device.

It is also possible though, to ignore the rewind operations which are caused by a door opening procedure without any cartridge changing, since the use and wear of the device is significantly lower when there was no complete cartridge spent and exchanged.

According to a next embodiment of the method according to the invention, one operation of the drive train is the run time of the electromechanical assembly.

The run time of the electromechanical assembly may be determined without any additional hardware configurations, for example by a timer or counter in the control unit. Generally, the run time is the time that the electromechanical assembly is operated. The run time may comprise both the forward and the backward movement of the electromechanical assembly and may also include the use of the device while no dosing operation takes place, for example by a user testing operation of the device, or simply playing with the device. The factor of this additional usage-time can be accounted for in this way, further improving the safety of the medical device.

Optionally, an estimation of the dispensed units can be performed on the basis of the run time, when the speed of the motor is known during the time. This additional information can be accounted for with weighting factors in the total run time, for example.

The operation of the drive train can also be the number of doses or units dispensed. While for the number of doses a smaller total number needs to be saved less frequently, for the number of units a more precise estimation of the use can be achieved.

According to another embodiment of the method according to the invention, one operation of the drive train is the power-cycle of the electromechanical assembly. Counting the number of power cycles, that means the number of on- and/or off-switching of the electromechanical assembly, the estimation of the usage can be further improved since the motor might be switched on and off independently from the medical device, for example for power saving. In case there are two motors provided for delivering two drugs, one of the motors might even be switched off during a dosing procedure, while the other drug is administered. By considering the power cycle of the electromechanical assembly an even more precise estimation of the use of the device with respect to the electromechanical assembly can be provided resulting in an improved safety of the medical device.

According to another embodiment according to the method according to the invention, a further criterion is that an operation of a cartridge changing procedure reaches or exceeds a limit.

Thus, the wear and use of the medical device is not only determined by the first and/or second criterion but also by a further criterion. By detecting the limit of use of the medical device further based on whether an operation of a cartridge changing procedure reaches or exceeds a limit, a further improvement of the precision of the use of the device can be achieved resulting in an improved safety.

In particular, an operation of a cartridge changing procedure is a door opening operation. For every cartridge change the opening of a door can be made necessary, providing the possibility to monitor and count the door opening in order to provide information about the device usage. Moreover it can be checked, whether a door opening operation is performed with or without an appropriate exchange of the cartridge. Since the use of the medical device is much larger when a complete cartridge was spent compared to the case where the door was only opened accidentally for example, this effect can be taken into account. Accidental door opening operations can be completely ignored, for example.

Moreover it is possible to estimate the number of spent units, since generally the content of the cartridges is known and due to the number of door opening operations followed by a cartridge exchange, the number of dispensed units can be estimated. This further improves the accuracy of the estimation of the wear and use of the medical device and thus the safety.

Alternatively, a door closing operation can be counted, as well. It is further possible to detect the cartridge itself and thus a cartridge change. Another operation of the cartridge changing procedure is a change of a dispense interface, for example, since they are usually exchanged together with the cartridge. For these operations the same advantages yield as for a door opening operation. The change of the cartridge itself can be counted, as well. For this purpose, the insertion or the unplugging of a cartridge can be mechanically and/or electronically detected.

According to a further embodiment of the method according to the invention a further criterion is that an operation of a charging process of the medical device reaches or exceeds a limit.

On the one hand, it is possible to count the charging time of a battery provided in a portable medical device, for example. When the device is primarily used with battery power the amount of charging is substantially proportional to the amount of use and wear of the device. The amount of power consumption can also be a measure for the power-on time of the main power consumers of the medical device, in particular display and electromechanical assembly. Additionally, information on the durability of the battery can be derived from the charging times. In this way a further improved estimate of the usage of the device can be derived, providing a better safety.

On the other hand, the number of charges can be counted. This is advantageous since no additional timer is necessary compared to when the charging time is measured. It is also possible to check for battery damages caused by a user charging after every dose delivery, for example.

According to another embodiment of the method according to the invention, a further criterion is that a power-on time reaches or exceeds a limit. By monitoring the power-on time of elements of the medical device an estimation of the usage of the medical device can be derived with little cost and alterations to the device.

It is possible, for instance, to provide the powered-up time of the device as a power-on time. This can be easily realized with triggering a timer with the power-button, for example. It is also conceivable to use the power-on time of a control unit, for example of a main microcontroller, as a measure for wear.

However it is more precise, when the power-on time of the electromechanical assembly, for example the motor or stepper motor, is used as a measure for the use, since generally the device can be turned on without actually using it, resulting in an overestimation, when the power on time of the whole device or a control unit is used.

It is also possible to use the display power-on time as a power-on time. This power-on time is also easy to implement and provides a good estimation of the use of the display. Risks arising from malfunctions of the display can be better estimated. Likewise, it is possible to provide the power-on time of an LED as a measure for the use. A timer can be triggered when the LED is switched on and the other way around, for example.

It is further possible to provide the further criterion that a user action reaches or exceeds a limit. Such a user action can be the pressing of a button, for example. The button pressing count is simple to implement and provides a good measure of the button durability directly and an approximate estimate of the state of the durability of the whole device.

Another possibility is to provide the removal or attaching of a cap of the device as a user action. This action could be measured by a cap detect switch, for example. Such a criterion would also provide a good estimate of the use of the device while a cap detect switch is simple to implement and fail-safe.

Door opening and closing operations of the medical device can also be seen as a kind of a countable user action.

According to a second aspect of the present invention, the technical problem is further solved by a medical device for performing a method according to the invention, comprising a reservoir containing a fluid, a drive train comprising an electromechanical assembly, a fluidic channel, a control unit, an indicator configured to indicate the limit of use of the medical device, a first sensor configured to detect the first use of the device, and at least a second sensor configured to detect at least one operation of the drive train of said medical device. The fluid is ejectable from the reservoir through the fluidic channel by a movement of the electromechanical assembly. The control unit and the sensors are configured such that the limit of use is reached when at least one of a first criterion and a second criterion is met.

By providing a control unit and sensors which determine, whether a limit of use is reached based not only a first criterion, but also a second criterion, the safety of the device can be significantly improved. By limiting at least one operation of a drive train an additional element of the usage of the medical device is taken into account for the detection of the limit of use of the medical device. A much more precise estimation of the wear and use of the device can be provided in this way resulting in the possibility to indicate the limit of use of the medical device earlier than the time limit of the first criterion and at the same time allowing the time limit of the first criterion to be set more generously without risking errors of the device due to wear and use, since these aspects are additionally considered by the second criterion.

The sensor for detecting the first use of the device can either be realized by hardware, such that a switch, for example a transistor, is activated the first time the device is turned on. The sensor can also be implemented in a control unit, for example the control unit of the medical device, such that when the control unit is switched on for the first time, the timer is activated. The timer can be implemented into the control unit as well, for example.

The second sensor for detecting at least one operation of the drive train of the medical device can be designed in various ways, mostly dependent on the kind of operation to be monitored. For example, when the movement of the electromechanical assembly needs to be monitored, a motion detector can be implemented. This motion detector can then detect the rewinds of an electromechanical assembly or the steps of a stepper motor. In case the run time of the electromechanical assembly is a criterion the sensor can also be implemented in the control unit or in a dedicated motor driver for example. Thus, the at least second sensor can also be realized by the control unit itself and does not necessarily need to be a separate sensor. In case there is more than one operation of the drive train to be detected, more sensors can also be provided.

According to the embodiments of the method according to the invention, in further embodiments of the medical device according to the invention further sensors can be provided. Such a sensor can in particular be an electronic circuit being able to detect power consumption of a certain element. Such elements can be a display, an electromechanical assembly, a control unit and/or a microcontroller, for example. This sensor can then trigger a counter or a timer, depending on whether a number or the time of a certain action is to be measured.

Such a sensor can further be any sort of actuator or trigger, for example to detect a movement of a cartridge, an opening or closing of a door, a removal or attaching of a cap or a dispense interface etc.

An indicator for indicating the limit of use is understood to be a user interface for instance, providing a perceivable signal to the user. Such a signal may be of any audio or visual or haptic kind, for example. To indicate the limit of use it is also possible to provide an indicator able to deactivate the medical device electronically or mechanically by a locking mechanism, for example.

The control unit is in particular able to compare the counted numbers of actions or operations or a measured time to limits set by the respective criterion.

It is further possible that multiple reservoirs containing a fluid each, multiple drive trains, in particular a drive train for each reservoir, comprising an electromechanical assembly each, multiple fluidic channel, multiple control units, multiple indicators indicating different or the same limit of use of the medical device and/or multiple sensors are provided.

It is especially preferred though, when two reservoirs are provided with a separate drive train each. In that case it is possible to detect a limit of use with respect to only one drive train and/or reservoir. If there is a relationship between the use of the two fluids or medicaments, the use and wear of the first drive train, for example, can be calculated or estimated from the use of the second or the other way around. Of course, it is also possible to detect a limit of use with respect to both drive trains and/or further elements, such as electromechanical assembly, cartridge door etc.

It is further advantageous, when a drug delivery device, in particular a portable drug delivery device, comprises a medical device according to the invention.

According to a third aspect of the present invention, further a program is disclosed comprising program code for performing the method according to the present invention and all exemplary embodiments thereof, when the program is executed on a processor.

The program may for instance be distributed via a network, such as for instance the Internet. The program may for instance be stored or encoded on a readable medium, for instance a computer-readable or processor-readable medium. The readable medium may for instance be embodied as an electric, magnetic, electro-magnetic, optic or other storage medium, and may either be a removable medium or a medium that is fixedly installed in an apparatus or device. The readable medium may for instance be a tangible medium, for instance a tangible storage medium.

BRIEF DESCRIPTION OF THE FIGURES

These as well as other advantages of various aspects of the present invention will become apparent to those of ordinary skill in the art by reading the following detailed description, with appropriate reference to the accompanying drawings, in which.

DETAILED DESCRIPTION

Figure 1A:
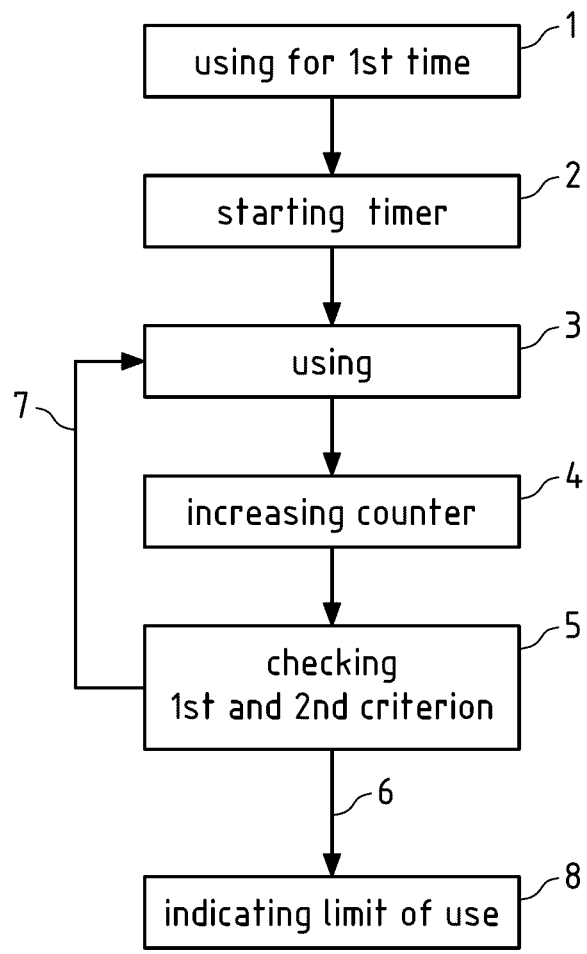
FIG. 1a-b show diagrams illustrating two exemplary embodiments of the method according to the invention.
Figure 2:
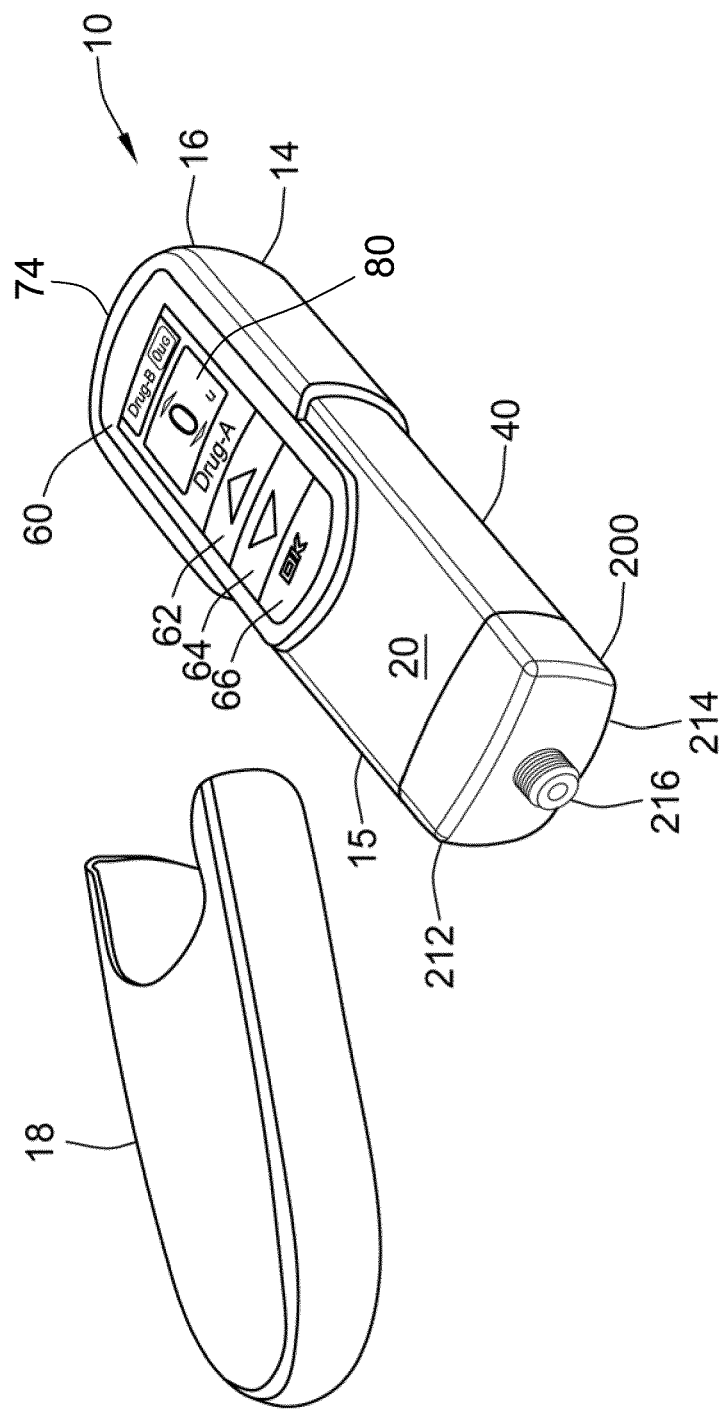
FIG. 2 illustrates a perspective view of a delivery device with an end cap of the device removed.
Figure 3:
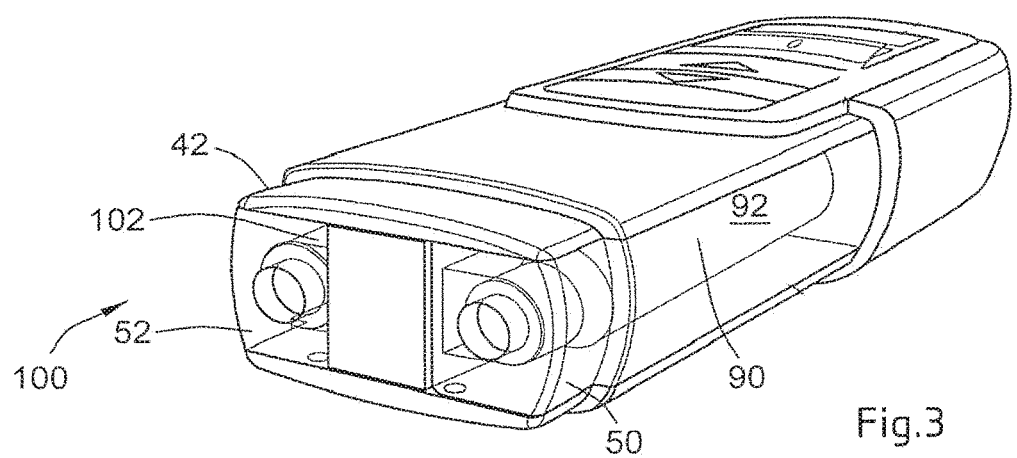
FIG. 3 illustrates a perspective view of the delivery device distal end showing the cartridge.

FIG. 1a shows a diagram illustrating a first exemplary embodiment of the method according to the invention. When a medical device for example the drug delivery device 10 as illustrated in FIG. 2, is used for the first time as illustrated in step 1, a timer is subsequently started according to step 2.

Used for the first time can mean that the device is switched on for the first time, that it is charged for the first time, that a cartridge is inserted for the first time etc. Generally every detectable step, that is performed, when the medical device is used, can be used as a trigger for the timer.

Figure 9:
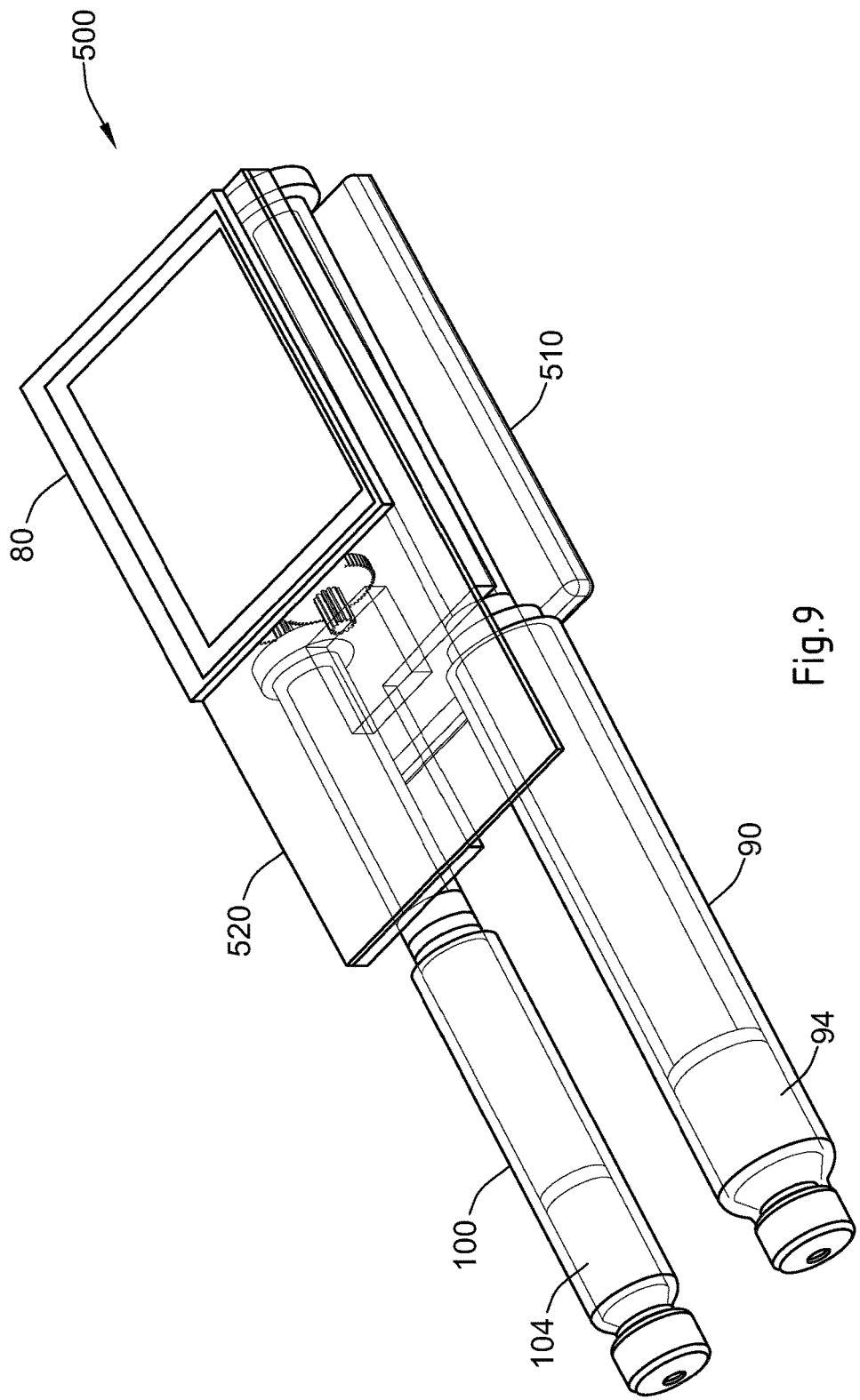
FIG. 9 illustrates a schematic view of a drive mechanism for use with the drug delivery device illustrated in FIG. 2.

After the timer has been started, the user begins and continues to use the device as intended, as it is illustrated in step 3. During this "using" of the medical device operations of one or multiple drive trains 500 (as illustrated in FIG. 9) of the medical device take place. Such operations can be the steps of a stepper motor or the motor rewind operations, for example. When during the using of the medical device a relevant operation of the drive train, which is part of the second criterion, is performed, in step 4 of FIG. 1*a* a counter is increased.

In this example, the counter is increased every time the according operation of the drive train is executed. It is alternatively possible, that the counter is only increased after certain time intervals or at certain events, for example. In that case step 4 may only be executed at the end of every day or after a cartridge change. Said counter can be managed by the control unit.

After the counter has been increased, it is checked whether at least one of the first and the second criterion is met. To check, whether the first criterion is met, a control unit may simply compare the current value of the timer (representing the time since the first use) with a time limit of for example 2 years. In order to check the second criterion, the control unit may observe or monitor whether the number of repetitions of a certain operation of the drive train reaches or exceeds a predefined limit.

If one of those criteria is fulfilled, the method proceeds along arrow 6 with step 8 and the limit of use of the medical device is indicated. This indication may be realized by displaying a warning on the display 80 in the control panel region 80 as illustrated in FIG. 2, for example. Alternatively or additionally the PCBA 520, 620 or electronic components on the PCB can be brought into a status inhibiting any further use of the medical device 10. If neither of the criteria is fulfilled, the method proceeds according to arrow 7 with the using of the medical device.

Figure 1B:
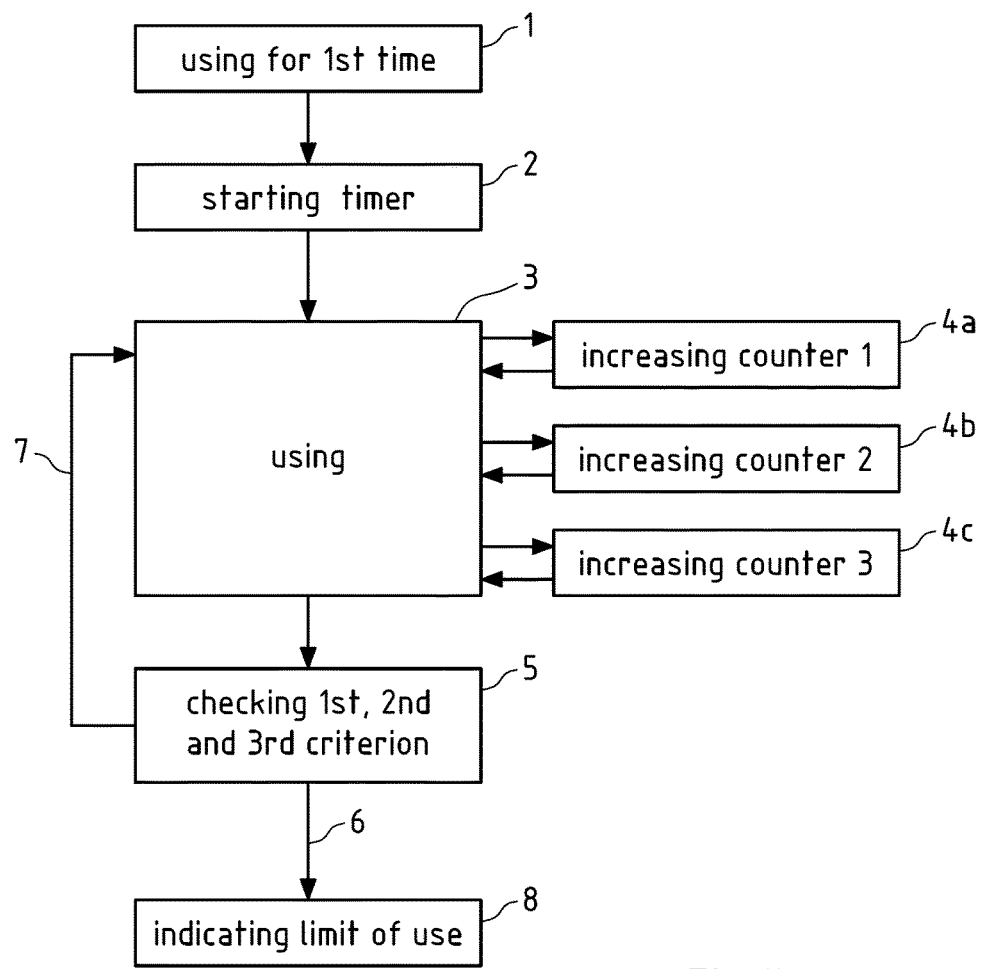

FIG. 1*b* shows a further diagram illustrating a second exemplary embodiment of the method according to the invention, which is similar to the embodiment shown in FIG. 1*a*. After the steps 1 and 2, according to which the first use of a medical device is detected and a timer is started, the medical device is used as normal by the user (step 3).

In contrast to the aforementioned example, according to this exemplary embodiment of the method according to the invention, not only a single operation of a drive train of the medical device is counted by increasing counter 1, but also a second operation of a drive train of the medical device is counted by increasing counter 2. For example, counter 1 may be increased in step 4*a*, when a rewind of a drive train takes place, while counter 2 may be increased in step 4*b* according to the runtime of the electromechanical device. As described above, the counter can be increased every time the according operation of the drive train is executed or it is possible, that the counter is only increased after certain time intervals or at certain events, for example. In this embodiment, counter 2 is a timer which represents the run time of the electromechanical device and which is started and stopped according to the starting and stopping of the electromechanical device. Counter 1 and counter 2 both count operations of a drive train of the medical device. They are both checked with respect to the first and second criterion. If one of the first or the second counter reaches its limit, the first or second criterion is regarded as fulfilled, and the process proceeds to step 8 indicating the limit or end of use of the medical device.

Additionally, there is, according to step 4*c*, another counter 3, which is increased according to a further operation of a part of the medical device, for example an operation of a cartridge changing process, such as a door opening, a door closing, an insertion or a take out of cartridge. A further (in this case a third) criterion is thus provided. If one of the first, second or the third counter reaches its limit, the first, second or third criterion is regarded as fulfilled, and the process proceeds to step 8 indicating the limit or end of use of the medical device.

In a further embodiment of the method according to the invention, the counters 1 to 3 can be increased without necessarily checking the criteria. The criteria can be checked according to step 5 of FIG. 1*b* independently of whether a counter is increased or not. Thus the criteria may only be checked once every day, for example. If one of the criteria 1 (timer reaches limit), 2 (at least one of the two operations of a drive train reaches or exceeds the its limit) or 3 (operation of a cartridge changing procedure reaches or exceeds its limit) is fulfilled, the method proceeds along arrow 6 with step 8 and the limit or end of use of the medical device is indicated. This indication may be realized by displaying a warning on the display 80 in the control panel region 80 as illustrated in FIG. 2, for example. Alternatively or additionally the PCBA 520, 620 or electronic components on the PCB can be brought into a status inhibiting any further use of the medical device 10. If neither of the criteria is fulfilled, the method proceeds according to arrow 7 with the using of the medical device.

Figure 1C:
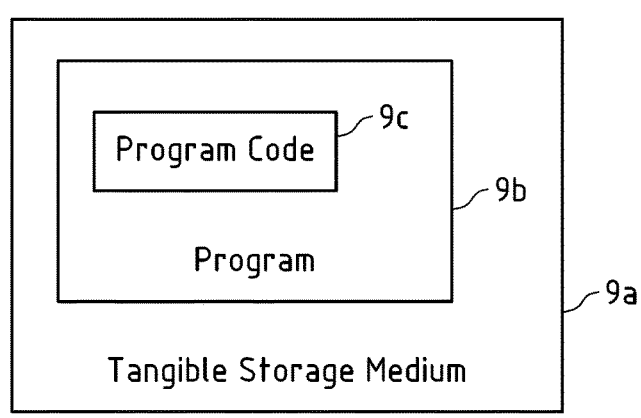
FIG. 1c schematically illustrates an exemplary embodiment of a tangible storage medium 9a according to the present invention.

FIG. 1*c* schematically illustrates an exemplary embodiment of a tangible storage medium 9*a* according to the present invention. Tangible storage medium 9*a* may for instance store a computer program 9*b*, with program code 9*c* for detecting a limit of use of a medical device comprising the steps of starting a timer of a medical device when the medical device is used for the first time, detecting the limit of use of the medical device, indicating the limit of use of the medical device, wherein the limit of use is reached when at least one of at least a first criterion and a second criterion is met, wherein the first criterion is that the timer reaches or exceeds a time limit and wherein the second criterion is that at least one operation of a drive train of the medical device reaches or exceeds a limit. Tangible storage medium 9*a* is a readable medium, for instance a computer-readable or processor-readable medium. Accordingly, the computer program 9*b* stored on tangible storage medium 9*a* may be executable by a computer or a processor. Tangible storage medium 9*a* may for instance be embodied as an electric, magnetic, electro-magnetic, optic or other tangible storage medium such as "read only memory" (ROM) or FLASH memory, and may either be a removable medium or a medium that is fixedly installed in an apparatus or device, such as for instance medical device 10 of FIG. 2.

The drug delivery device illustrated in FIG. 2 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body. Additionally, the attaching or removal of the cap 18 can be detected by an actuator implemented in the main body 14 in order to count the number of cap removals and/or attachments so that this number can be used in order to check the criterion whether a limit of an operation of a cartridge changing procedure is exceeded or reached.

The main body 14 contains a control unit in form of a micro-processor control unit, two electro-mechanical drive trains, and at least two medicament reservoirs. When the end cap or cover 18 is removed from the device 10 (as illustrated in FIG. 2), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly. The exchange of the dispense interface 200 can also be used as an operation of the cartridge changing procedure even though the dispense interface 200 must not necessarily be exchanged during a cartridge change.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted. The retraction of the piston rod can be used as an operation of the drive train for the second criterion, for example.

A control panel region 60 is provided near the proximal end of the main body 14. Preferably, this control panel region 60 comprises a digital display 80 along with a plurality of human interface elements that can be manipulated by a user to set and inject a combined dose. The power on time of the display can be used as a measure for a power-on time. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 2). The buttons can be used as actuators for measuring a user action. In case the number of buttons pressed exceeds a limit, a criterion for a limit of use might be reached, indicating the limit of use.

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament. The cartridge holder 40, the main body 14 and/or the cartridge retainers 50, 52 may comprise sensors in form of actuators to detect a cartridge and thus also detect a cartridge change, providing a further possibility for an operation of a cartridge changing process.

In addition, at the distal end of the cartridge holder 40, the drug delivery device illustrated in FIG. 2 includes a dispense interface 200. As will be described in relation to FIG. 5, in one arrangement, this dispense interface 200 includes a main outer body 212 that is removably attached to a distal end 42 of the cartridge housing 40. As can be seen in FIG. 2, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 2 illuminates and provides the user certain device information, preferably information relating to the medicaments contained within the cartridge holder 40. For example, the user is provided with certain information relating to both the primary medicament (Drug A) and the secondary medicament (Drug B).

Figure 4:
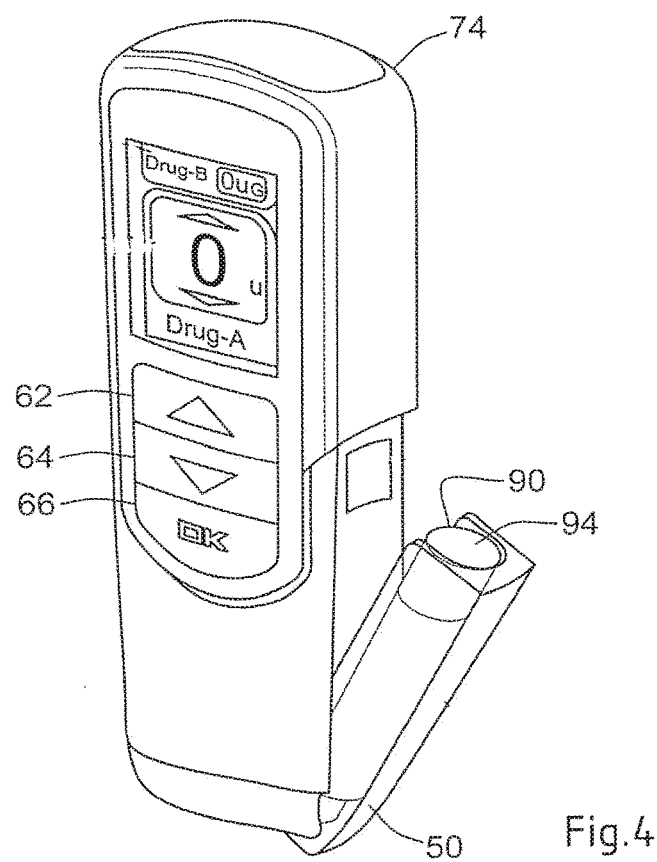
FIG. 4 illustrates a perspective view of the delivery device illustrated in FIG. 2 or 3 with one cartridge retainer in an open position.

As shown in FIG. 4, the first and second cartridge retainers 50, 52 may be hinged cartridge retainers. These hinged retainers allow user access to the cartridges. FIG. 4 illustrates a perspective view of the cartridge holder 40 illustrated in FIG. 2 with the first hinged cartridge retainer 50 in an open position. FIG. 4 illustrates how a user might access the first cartridge 90 by opening up the first retainer 50 and thereby having access to the first cartridge 90.

Figure 5:
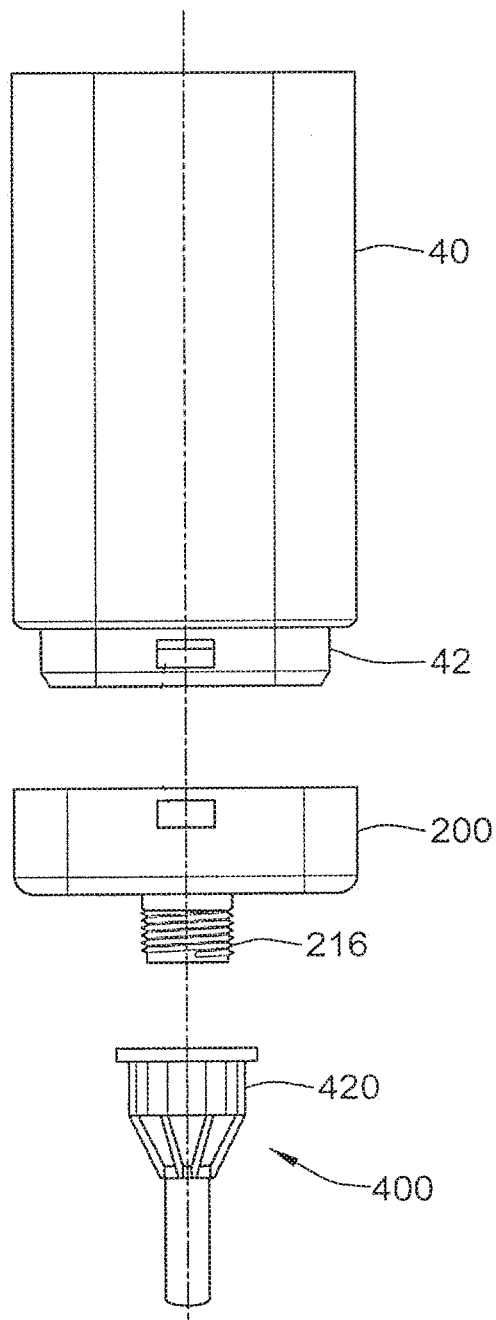
FIG. 5 illustrates a dispense interface and a dose dispenser that may be removably mounted on a distal end of the delivery device illustrated in FIG. 2.

As mentioned above when discussing FIG. 2, a dispense interface 200 is coupled to the distal end of the cartridge holder 40. FIG. 5 illustrates a flat view of the dispense interface 200 unconnected to the distal end of the cartridge holder 40. A dose dispenser or needle assembly that may be used with the interface 200 is also illustrated and is provided in a protective outer cap 420.

Figure 6:
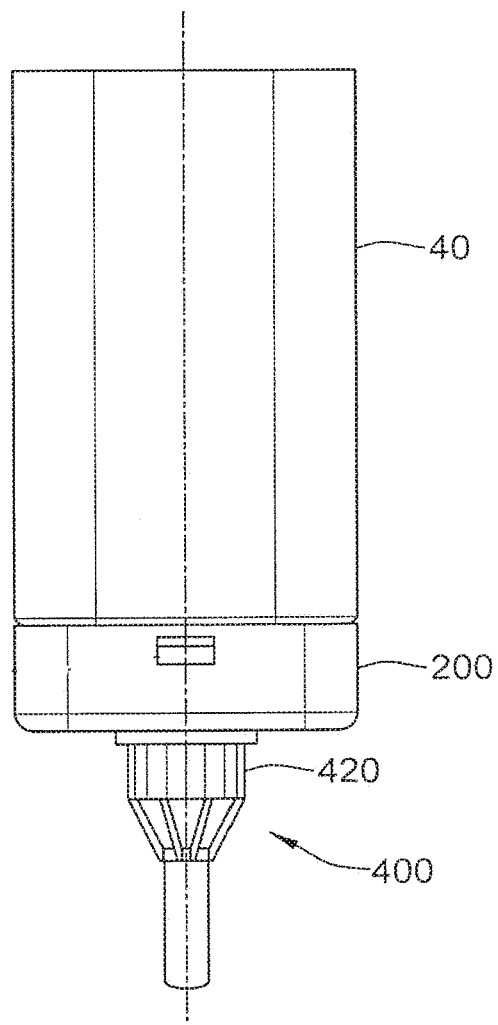
FIG. 6 illustrates the dispense interface and the dose dispenser illustrated in FIG. 5 mounted on a distal end of the delivery device illustrated in FIG. 2.

In FIG. 6, the dispense interface 200 illustrated in FIG. 5 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device. In particular, such additional features can be sensors which count the number of cartridge changes.

Figure 7:
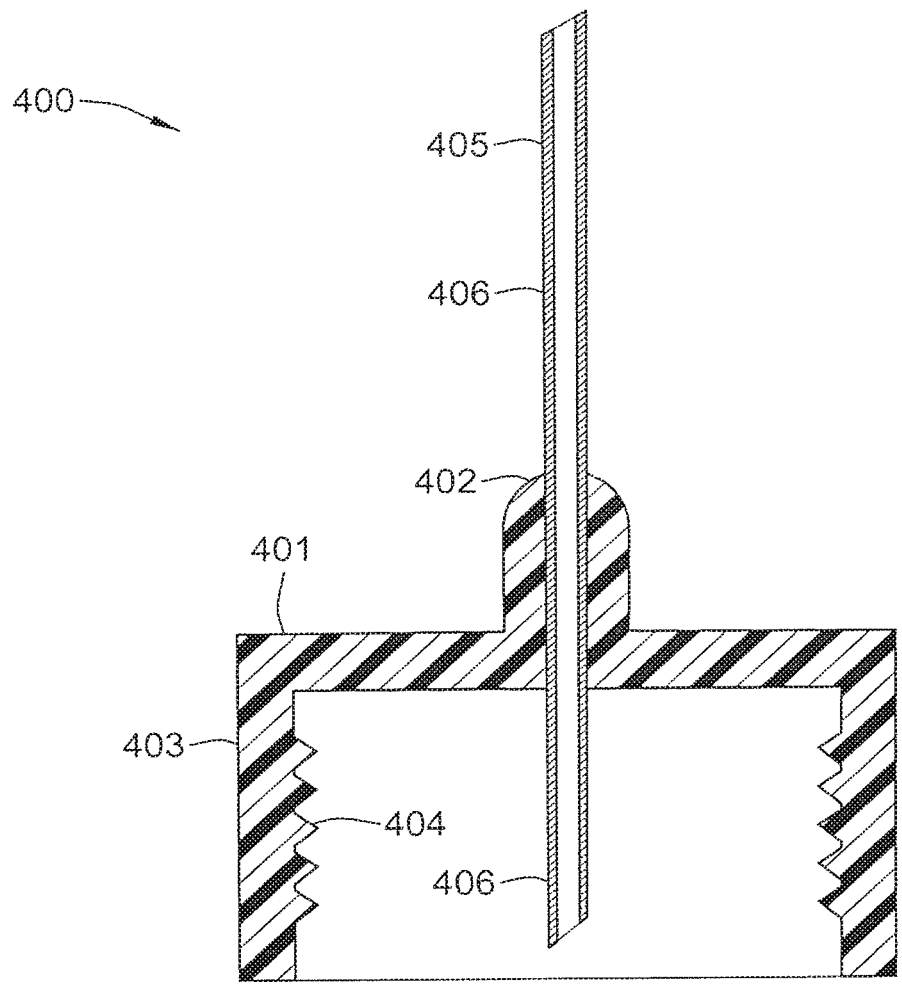
FIG. 7 illustrates one arrangement of a needle assembly that may be mounted on a distal end of the delivery device.

FIG. 6 also illustrates the needle assembly 400 and protective cover 420 coupled to the distal end of the dispense interface 200 that may be screwed onto the needle hub of the interface 200. FIG. 7 illustrates a cross sectional view of the double ended needle assembly 402 mounted on the dispense interface 200 in FIG. 6.

The needle assembly 400 illustrated in FIG. 7 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 406 of the needle assembly 400 protrudes from an opposite side of the circular disc so that it is concentrically surrounded by the sleeve 403. In one needle assembly arrangement, the second or proximal piercing end 406 may be shorter than the sleeve 403 so that this sleeve to some extent protects the pointed end of the back sleeve. The needle cover cap 420 illustrated in FIGS. 5 and 6 provides a form fit around the outer surface 403 of the hub 401.

Figure 8:
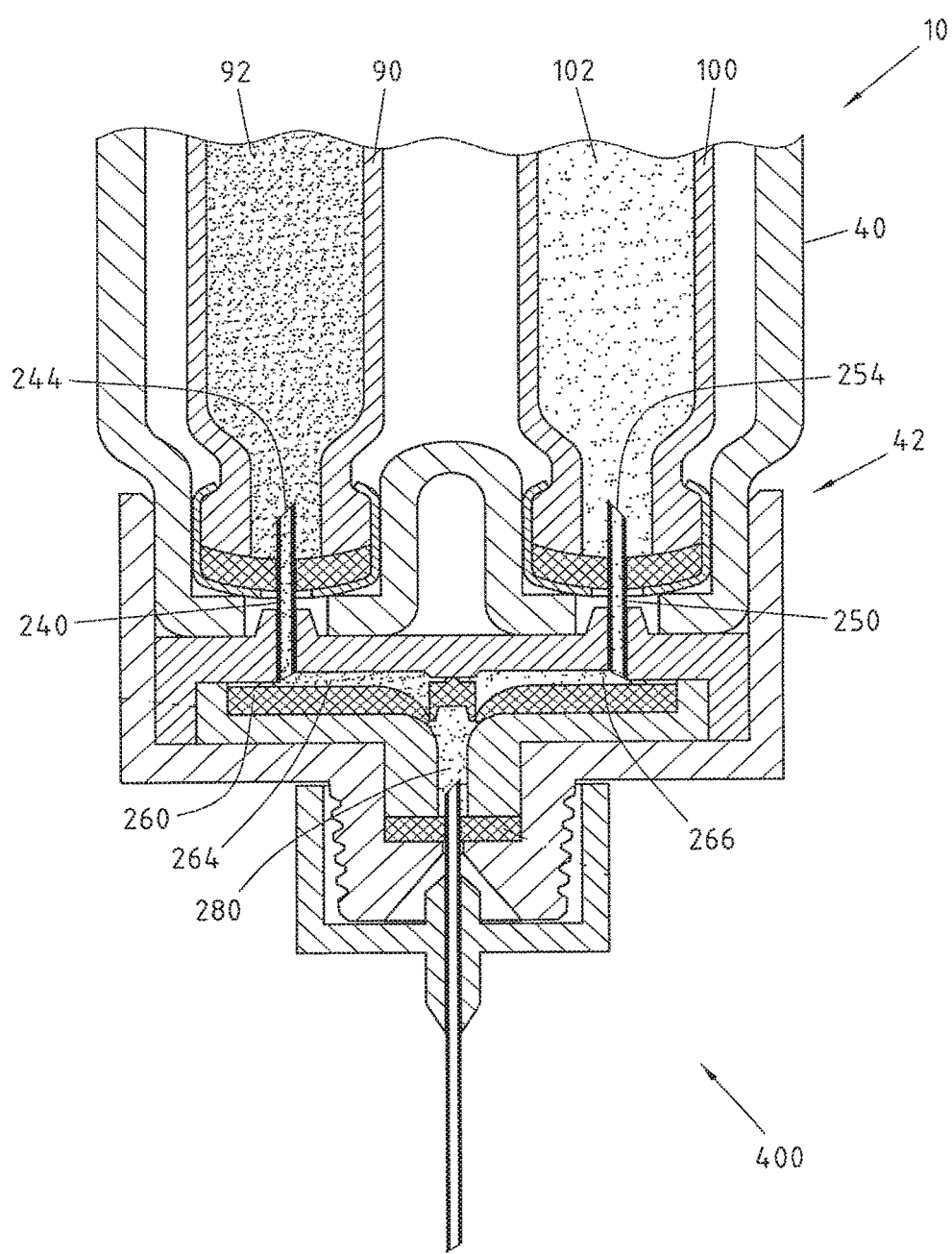
FIG. 8 illustrates a cross-sectional view of the dispense interface and needle assembly mounted onto a drug delivery device, such as the device illustrated in FIG. 2.

FIG. 8 illustrates the dispense interface 200 after it has been mounted onto the distal end 42 of the cartridge holder 40 of the drug delivery device 10 illustrated in FIG. 2. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 8 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 8, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 8, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

FIG. 9 illustrates various internal components of the drug delivery device 10 illustrated in FIG. 2 including one preferred arrangement of drive trains 500. An operation of these drive trains is monitored by means of a motion detector system, so that a limit of use can be detected, as will be shown in FIGS. 10 and 11 in particular. As illustrated, FIG. 9 illustrates the digital display 80, a control unit in form of a printed circuit board assembly (PCBA) 520, along with a power source or battery 510. Charging processes of the battery source, such as charging time and/or charging count, are preferably monitored in order to provide data, which can be compared to a criterion, which is a limited operation of a charging process. The PCBA 520 may be positioned between the digital display 80 and drive trains 500 with the battery or power source 510 positioned beneath these drive trains. The PCBA may in particular be responsible for the detection, whether a limit of use has been reached or exceeded. The PCBA can in particular comprise the timer, which is activated, when the medical device 10 is used for the first time. The timer counts continuously counts seconds for 2 years, for example. When, for example, 63,072,000 seconds are reached, the criterion for the timer having reached its limit is fulfilled leading to the indication of the limit of use. The device can either not be operable anymore, or a warning might be output to the user. The battery or power source 510 is electronically connected to provide power to the digital display 80, the PCBA 520 and the drive trains 500. As illustrated, both the first and second cartridges 90, 100 are shown in an expended state. That is, the first and second cartridges are illustrated in an empty state having a stopper at a most distal position. For example, the first cartridge 90 (which ordinarily contains the first medicament 92) is illustrated as having its stopper 94 in the distal position. The stopper 104 of the second cartridge 100 (ordinarily containing the second medicament 102) is illustrated in a similar position.

With reference to FIG. 9, it may be seen that there is provided a first region defining a suitable location for a power source 510 such as a replaceable battery or batteries. The power source 510 may comprise a rechargeable power source and may be recharged while the power source 510 remains in the device. Alternatively, the power source 510 may be removed from the drug delivery device 10 and recharged externally, for example, by way of a remote battery charger. This power source may comprise a Lithium-Ion or Lithium-polymer power source. In this preferred arrangement, the battery 510 comprises a generally flat and rectangular shaped power source.

Figure 10:
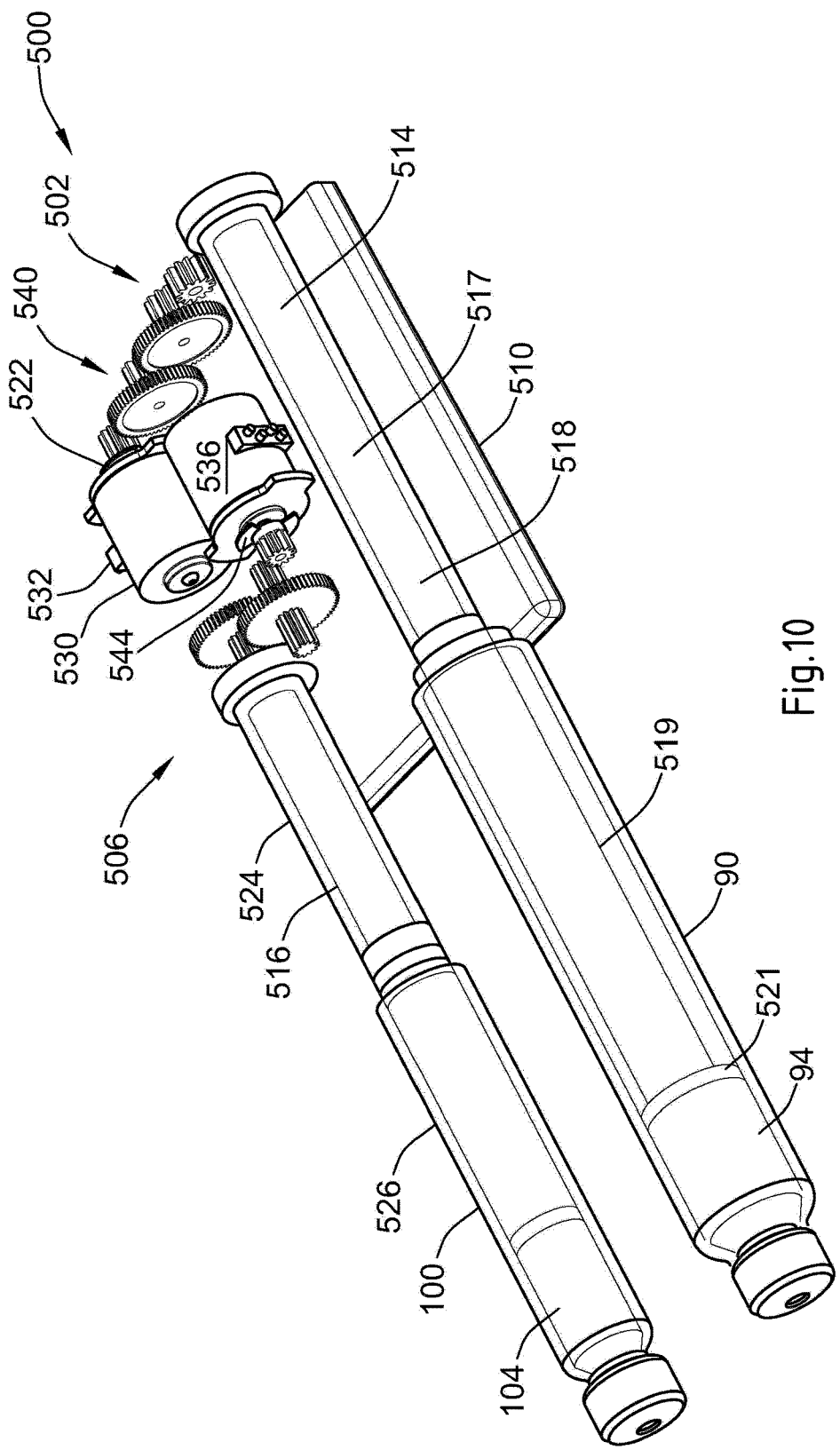
FIG. 10 illustrates another schematic view of the drive mechanism illustrated in FIG. 9.

FIG. 10 illustrates the first arrangement of the electro-mechanical system illustrated in FIG. 9 with both the digital display 80 and the PCBA 520 omitted. As illustrated in FIG. 10, the drive trains 500 operate to expel a dose from the first cartridge 90 containing the primary medicament 92 and the second cartridge 100 containing the secondary medicament 102. The first drive train roughly consists of a first mechanical driver 502 with a first motor 530, a first gearing arrangement 540 and a first piston rod 514, while the second drive train roughly consists of a second mechanical driver 506 with a second motor 536, a second gearing arrangement and a second piston rod 516. Again, as illustrated in FIG. 10, the first and second cartridges 90, 100 are illustrated in an empty state having stoppers at a most distal position.

In this preferred electro-mechanical system 500, the system comprises an independent mechanical driver for each cartridge 90, 100. That is, an independent mechanical driver 502 operates to expel a dose from the first cartridge 90 and an independent mechanical driver 506 operates to expel a dose from the second cartridge 100. In an alternative drive train system operating on three different medicaments, three independent mechanical drivers could be provided. The independent mechanical drivers may act under control of motor drivers of a control unit like the PCBA 520.

The first independent mechanical driver 502 operates to expel a dose from the first cartridge 90. This first driver 502 comprises a first motor 530 that is operatively coupled to a first gearing arrangement 540. To energize this motor 530, a connector 532 is provided as a means of electrically connecting to a motor driver. Operating signals can also be sent to the motor 530 via this connector. The requested movement of the motor can be used as an operation of a drive train in order to monitor the movement of the motor and to detect a limit of use. This first gearing arrangement 540 is mechanically linked to a proximal portion of the first telescoping piston rod 514. The first telescoping piston rod 514 is illustrated in a fully extended position having a distal end 521 acting on the stopper 94 of the first cartridge 90.

As this gearing arrangement 540 is driven by the output shaft of the first motor 530, this arrangement 540 rotates the proximal portion 518 of the first telescoping piston rod 514. As this proximal portion 518 of the piston rod 514 is rotated, the second or distal portion 519 of the piston rod 514 is driven in a distal direction.

Preferably, the proximal portion 518 of the telescope piston rod 514 comprises an external thread 517. This thread 517 engages the distal portion 519 which has in integrated nut comprising a short threaded section at a proximal end of the distal portion 519. This distal portion 519 is prevented from rotating via a key acting in a keyway. Such a keyway may pass through the middle of first telescope 514. Therefore, when the first gearbox arrangement 540 causes rotation of the proximal section 518, rotation of the proximal portion 518 acts upon the distal end 521 to thereby drive the distal portion of telescope piston rod to extend along the longitudinal axis.

Moving in this distal direction, the distal end 521 of the second portion 519 of the piston rod 514 exerts a force on a stopper 94 contained within the first cartridge 90. With this distal end 521 of the piston rod 514 exerting a force on the stopper, the user selected dose of the first medicament 92 is forced out of the cartridge 90 and into an attached dispense interface 200 and consequently out an attached needle assembly 400 as previously discussed above.

A similar injection operation occurs with the second independent driver 506 when a controller, such as the control unit or another independent controller, first determines that a dose of the second medicament 102 is called for and determines the amount of this dose. As previously mentioned, in certain circumstances, the controller may determine that a dose of the second medicament 102 may not be called for and therefore this second dose would be "set" to a "0" dose.

Preferably, motors 530, 536 comprise motors suitable for electronic commutation. Most preferably, such motors may comprise either a stepper motor or a brushless DC motor.

To inject a dose of the primary and secondary medicaments 92, 102, a user will first select a dose of the primary medicament by way of the human interface components on the display 80. (see, e.g., FIGS. 1 and 4). After a dose of the drug from the primary medicament 92 has been selected, the microcontroller will utilize a previously stored algorithm for determining the dose size of a second drug 102 from a second medicament cartridge. This pre-defined algorithm may help to determine at least in part the dose of the second medicament 102 based on a pre-selected therapeutic profile. In one arrangement, these therapeutic profiles are user selectable. Alternatively, these therapeutic profiles may be password protected and selectable only by a person authorized with the password, such a physician or patient care giver. In yet another arrangement, the therapeutic profile may only be set by the manufacture or the supplier of the drug delivery device 10. As such, the drug delivery device 10 may be provided with only one profile.

When the dose sizes of the first and second medicaments have been established, the user can press the injection button 74 (see e.g., FIG. 2). By pressing this button 74, the motor drivers 332, 334 energize both the first and the second motors 530, 536 to begin the injection process described above.

The piston rods 514, 516 are preferably movable between a first fully withdrawn position (not shown) and a second fully extended portion (as shown in FIGS. 22 and 23). With the piston rods 514, 516 in the withdrawn position, the user will be allowed to open up the respective cartridge retainer and remove an empty cartridge. In one preferred arrangement, an end stop switch may be provided in the main body 14 of the drug delivery device 10 so as to detect when either or both of the piston rods 514, 516 are in a fully withdrawn position. Tripping of the end stop switch may release a catch or other fastening device so as to allow access to the main body for replacement of either cartridge 90, 100. Additionally, this switch can be used to count the number of cartridge exchanges. Furthermore it is possible to estimate the number of units dispensed with the medical device 10.

In one preferred arrangement, both the first and second motors 530, 536 operate simultaneously so as to dispense the user selected dose of the first medicament 92 and the subsequently calculated dose of the second medicament 102 simultaneously. That is, both the first and the second independent mechanical drivers 502, 506 are capable of driving the respective piston rods 514, 516 either at the same or a different time. In this manner, now referring to the dispense interface 200 previously discussed, the first medicament 92 enters the holding chamber 280 of the dispense interface 200 at essentially the same time as the second medicament. One advantage of such an injecting step is that a certain degree of mixing can occur between the first and second medicament 92, 102 prior to actual dose administration.

If after an injection, the patient determines that one or more of the cartridges 90,100 is spent and therefore needs to be exchanged, the patient can follow the following method of cartridge exchange:

Remove the double ended needle from the dispense interface 200;

Remove the dispense interface 200 from the cartridge holder 40 of the device 10;

Enable a menu option on the digital display 80 to change the first cartridge 90 and/or the second cartridge 100;

Rewind the first and/or the second piston rods 514, 516;

The first and/or second cartridge retainer doors will pop open;

The user removes the spent cartridge and replaces this spent cartridge with a new cartridge;

The reservoir doors may manually be closed;

Once the doors are closed, the first and second piston rods 514, 516 advance so that a most distal portion of each rod will meet the stopper of the respective cartridge and will stop advancing when a bung detect mechanism coupled to the micro-processor is activated;

The user replaces the dispense interface 200 in the one way manner on the cartridge holder 40;

The user can, optionally, connect a new double ended needle to the dispense interface 200;

The user can, optionally, perform a test shot or a priming step with the device 10; and The user can then set the next dose for a subsequent dose administration step.

One or more of the steps may be performed automatically, for example controlled by microcontroller 302, such as the step of rewinding the first and/or second piston rod. It is possible to provide adequate sensors to count any of the above mentioned steps in order to compare them to a limit and decide whether a limit of use has been reached.

In an alternative arrangement, the controller may be programmed so that the first and the second independent mechanical drivers 502, 506 may be operated to dispense either the first medicament 92 or the second medicament 102 prior to the other medicament. Thereafter, the second or the primary medicament may then be dispensed. In one preferred arrangement, the secondary medicament 102 is dispensed before the primary medicament 92.

Preferably, the first and second motors 530, 536 comprise electronic commutation. Such commutation may help to minimise the risk of a motor runaway condition. Such a motor runaway condition could occur with a system comprising a standard brushed motor experiencing a fault. In one embodiment of the motor drive system, a watchdog system may be provided. Such a system has the ability to remove power to either or both of the motors in the event of a software malfunction or a failure of the electronic hardware. To prevent the power from being removed, the correct input from a number of sections of the electronic hardware and/or the microcontroller software will need to be provided. In one of these input parameters is incorrect; power may be removed from the motor.

In addition, preferably both motors 530, 536 may be operated in a reverse direction. This feature may be required in order to allow the piston rods 514, 516 to be moved between a first and a second position.

Preferably, the first independent drive train 502 illustrated in FIG. 10 comprises a first motion detection system 522 to be able to detect a limit of use with respect to an operation of the drive trains 500.

Figures 11A, 11B:
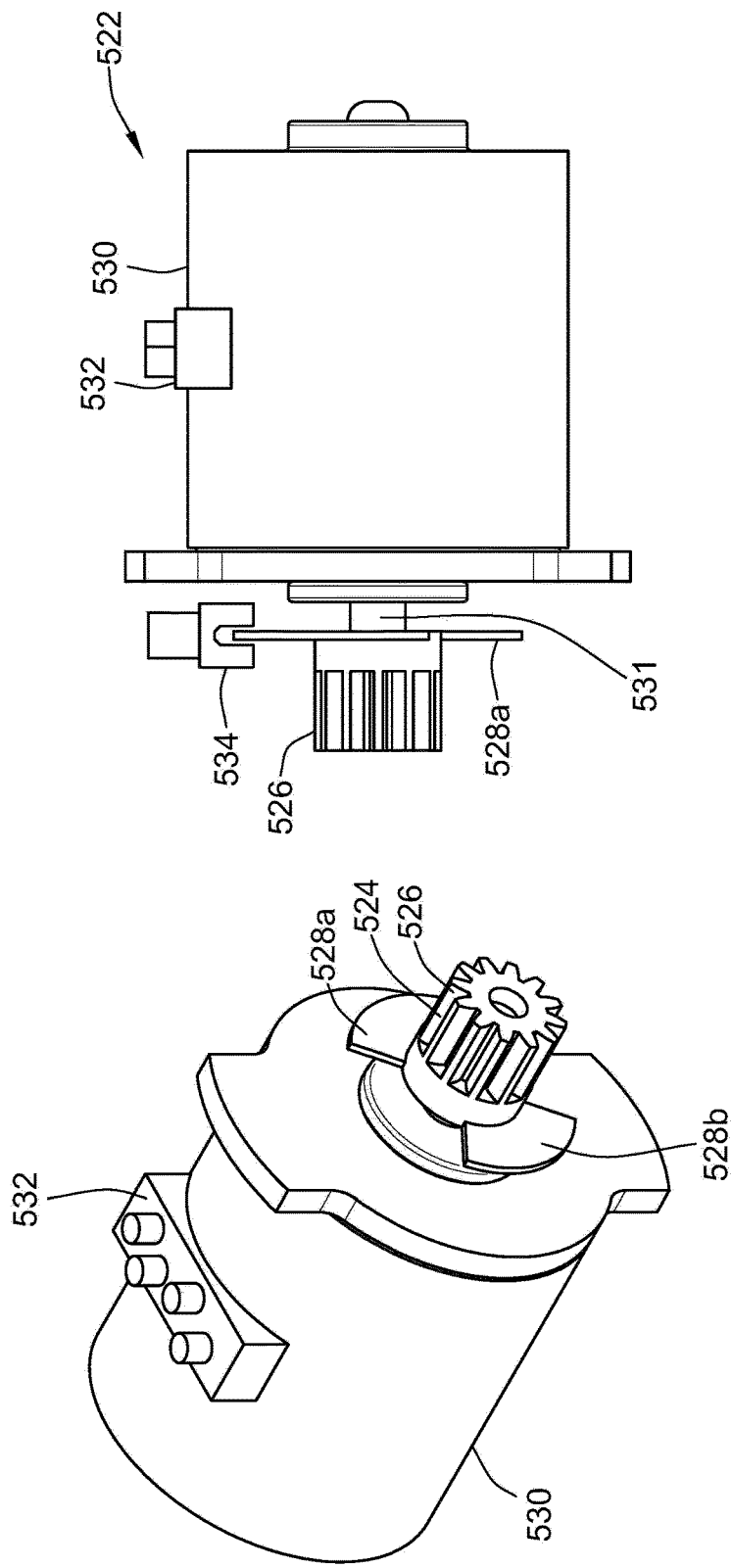
FIG. 11 illustrates two views of a motion detection system that may be used with the drive mechanism illustrated in FIG. 9.

FIG. 11a illustrates a perspective view of the first motor 530 illustrated in FIG. 10. FIG. 11b illustrates a preferred motion detection system 522 comprising the first motor 530 illustrated in FIG. 11a in conjunction with a digital encoder 534.

As illustrated in FIGS. 24a and 24b, such a motion detection system 522 may be beneficial as it can be utilized to provide operational and positional feedback from the first independent driver 502 to the control unit of the drug delivery device 10. The control unit can, for example, either compare a total movement of the motor to a limit, it can calculate steps performed by the stepper motor form the movement of the device or it can calculate units dispensed by the medical device form the detected movement. For example, with respect to the first independent driver 502, a preferred motion detection system 522 may be achieved through the use of a first motor pinion 524. This first pinion 524 operatively coupled to an output shaft 531 of the first motor 530. The first pinion 524 comprises a rotating gearing portion 526 that drives a first gear of the first gearing arrangement 540 (see, e.g., FIG. 10). The first motor pinion 524 also comprises a plurality of flags 528 a-b. In this first motion detection system arrangement 522, the first pinion 524 comprises a first flag 528a and a second flag 528b. These two flags 528a-b are positioned on the motor pinion 524 so that they pass through a first optical encoder 534 as the motor output shaft 531 and hence the connected first pinion 524 rotate when the motor is driven.

Preferably, as the first and second flags 528a-b pass through the first optical encoder 534, the encoder 534 can send certain electrical pulses to the microcontroller. Preferably, the optical encoder 534 sends two electrical pulses per motor output shaft revolution to the microcontroller. As such, the microcontroller can therefore monitor motor output shaft rotation. This may be furthermore advantageous to detect position errors or events that could occur during a dose administration step such as jamming of the drive train, incorrect mounting of a dispense interface or needle assembly, or where there is a blocked needle.

Preferably, the first pinion 524 comprises a plastic injection molded pinion. Such a plastic injection molded part may be attached to the output motor shaft 531. The optical encoder 534 may be located and attached to a gearbox housing. Such a housing may contain both the first gearing arrangement 540 along with the optical encoder 534. The encoder 534 is preferably in electrical communication with the control unit potentially via a flexible portion of the PCB. In a preferred arrangement, the second independent drive train 506 illustrated in FIGS. 22 and 23 comprises a second motion detection system 544 that operates in a similar fashion as the first motion detection system 522 of the first drive train 502.

Figure 12:
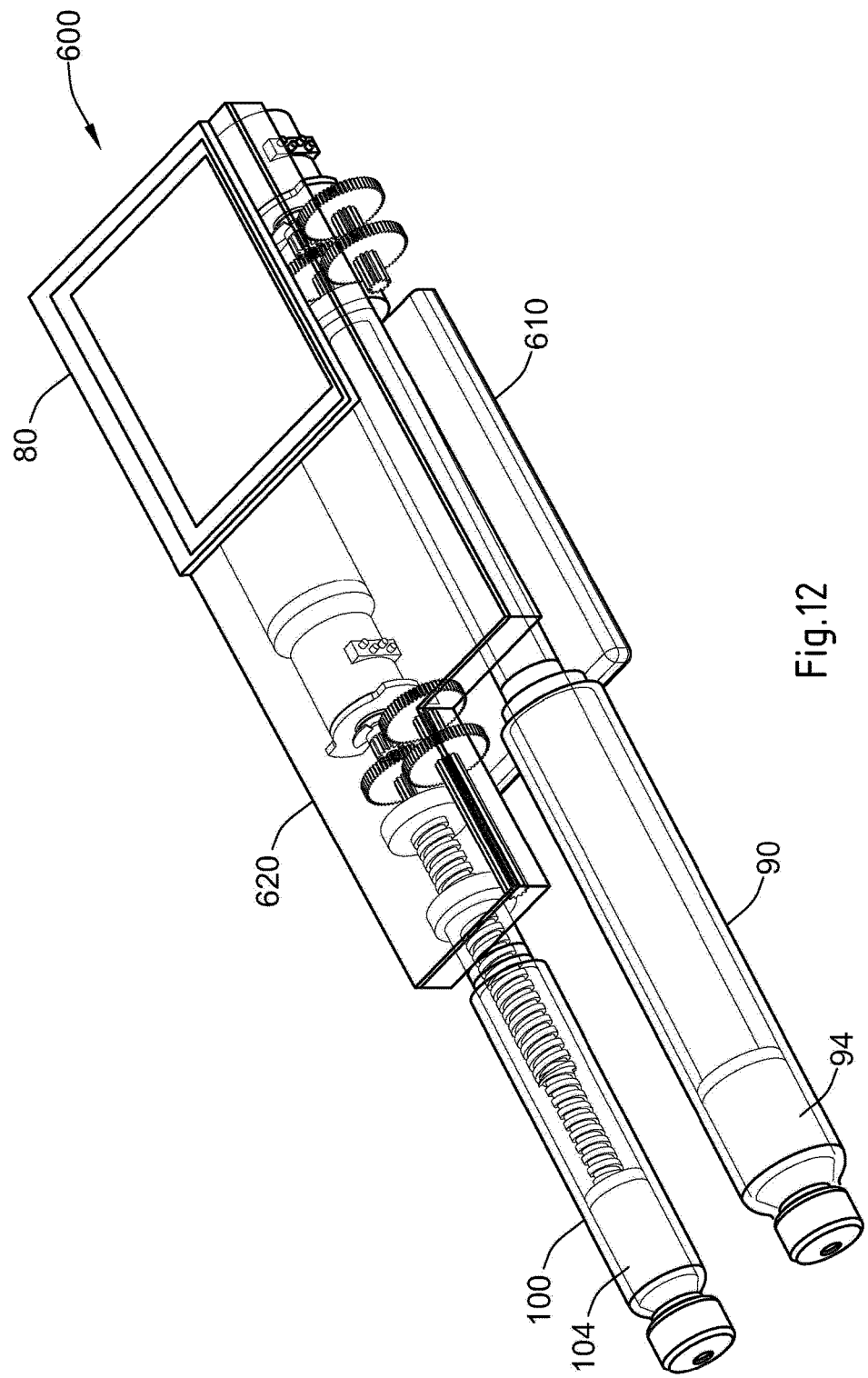
FIG. 12 illustrates a schematic view of an alternative drive mechanism for use with the drug delivery device illustrated in FIG. 2.

FIG. 12 illustrates various internal components of the drug delivery device 10 illustrated in FIG. 2 including a preferred alternative drive train arrangement 600. As illustrated, FIG. 12 illustrates the digital display 80, a printed circuit board assembly (PCBA) 620, along with a power source or battery 610. The PCBA 620 may be positioned between the digital display 80 and drive trains 600 with the battery or power source 610 positioned beneath this drive train. The battery or power source 610 is electronically connected to provide power to the digital display 80, the PCBA 620 and the drive train 600. The digital display 80 and the PCBA 620 of this alternative drive train arrangement 600 operate in a similar manner as previously described.

As illustrated, both the first and second cartridges 90, 100 are shown in an expended state. That is, the first and second cartridges are illustrated in an empty state having a stopper at a most distal position. For example, the first cartridge 90 (which ordinarily contains the first medicament 92) is illustrated as having its stopper 94 at the end or most distal position. The stopper 104 of the second cartridge 100 (ordinarily containing the second medicament) is illustrated in a similar end position.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB 29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2(25, Asp28] Exendin-4(1-39),
des Pro36 [Trp(O2(25, IsoAsp28] Exendin-4(1-39),
des Pro36 [Met(O)14 Trp(O2(25, Asp28] Exendin-4(1-39),
des Pro36 [Met(O)14 Trp(O2(25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2(25, Asp28] Exendin-4(1-39),
des Pro36 [Trp(O2(25, IsoAsp28] Exendin-4(1-39),
des Pro36 [Met(O)14 Trp(O2(25, Asp28] Exendin-4(1-39),
des Pro36 [Met(O)14 Trp(O2(25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2(25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2(25, Asp28] Exendin-4(1-39)-NH2,
H-Asn-(Glu)5-des Pro36, Pro37, Pro38 [Trp(O2(25, Asp28] Exendin-4(1-39)-NH2,
des Pro36, Pro37, Pro38 [Trp(O2(25, Asp28] Exendin-4(1-39)-(Lys)6-NH2,
H-(Lys)6-des Pro36, Pro37, Pro38 [Trp(O2(25, Asp28] Exendin-4(1-39)-(Lys)6-NH2,
H-Asn-(Glu)5-des Pro36, Pro37, Pro38 [Trp(O2(25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2(25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2 (25, Asp28] Exendin-4(1-39)-NH2,
des Pro36, Pro37, Pro38 [Met(O)14, Trp(O2(25, Asp28] Exendin-4(1-39)-(Lys)6-NH2,
H-(Lys)6-des Pro36, Pro37, Pro38 [Met(O)14, Trp(O2(25, Asp28] Exendin-4(S1-39)-(Lys)6-NH2,
H-Asn-(Glu)5-des Pro36, Pro37, Pro38 [Met(O)14, Trp(O2 (25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A method for limiting use of a medical device, the method comprising:
    starting a timer of the medical device when said medical device is used for a first time,
    checking whether a first criterion is met, wherein said first criterion is that said timer reaches or exceeds a time limit,
    checking whether a second criterion is met, wherein said second criterion is that at least one operation of a drive train of said medical device reaches or exceeds a limit, wherein the drive train comprises a stepper motor, and wherein one operation of said at least one operation of said drive train is a number of steps of the stepper motor during both dispense and rewind operations,
    detecting a limit of use of said medical device, wherein said limit of use is reached when either or both of the first criterion and the second criterion is met, and
    in response to that said limit of use has been reached, indicating said limit of use of said medical device.

2. The method according to claim 1, wherein the at least one operation of said drive train is a run time of the stepper motor.

3. The method according to claim 1, wherein the at least one operation of said drive train is a power-cycle of said stepper motor.

4. The method according to claim 1, wherein a further criterion is that an operation of a cartridge changing procedure reaches or exceeds a limit, wherein the operation of the cartridge changing procedure is selected from the group consisting of a door opening, a door closing, a cartridge change, and a dispense interface change.

5. The method according to claim 1, wherein a further criterion is that an operation of a charging process of said medical device reaches or exceeds a limit.

6. The method according to claim 1, wherein a further criterion is that a power-on time reaches or exceeds a limit.

7. The method according to claim 1, wherein a further criterion is that a user action reaches or exceeds a limit.

8. A medical device comprising
    a reservoir containing a fluid,
    a drive train comprising an electromechanical assembly,
    a fluidic channel,
    a control unit,
    an indicator configured to indicate a limit of use of said medical device,
    a first sensor configured to detect a first use of said medical device, a timer configured to start upon detecting the first use of said medical device and at least a second sensor configured to detect at least one operation of a stepper motor of said medical device, wherein said fluid is ejectable from said reservoir through said fluidic channel by a movement of said stepper motor, wherein said control unit is configured to both check whether a first criterion is met, wherein said first criterion is that the timer reaches or exceeds a time limit, and whether a second criterion is met, wherein said second criterion is that at least one operation of the stepper motor of said medical device reaches or exceeds a limit, wherein one operation of said at least one operation of said drive train is a number of steps of the stepper motor during both dispense and rewind operations, wherein said control unit is configured to detect that said limit of use is reached when either or both of said first criterion and said second criterion is met, and wherein said indicator is configured to indicate said limit of use of said medical device in response to said control unit detecting that said limit of use is reached.

9. A portable drug delivery device, comprising the medical device according to claim 8.

10. A non-transitory computer readable medium having instructions stored thereon that, in response to execution by a processor, cause the processor to perform the method according to claim 1.

* * * * *